US00PP18909P2

(12) United States Plant Patent
Egger

(10) Patent No.: US PP18,909 P2
(45) Date of Patent: Jun. 10, 2008

(54) ***CORYDALIS* PLANT NAMED 'CANARY FEATHERS '**

(50) Latin Name: *Corydalis hybrid*
Varietal Denomination: Canary Feathers

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 52 days.

(21) Appl. No.: 11/639,123

(22) Filed: Dec. 13, 2006

(51) Int. Cl.
*A01H 5/00* (2006.01)

(52) U.S. Cl. ..... Plt./373

(58) Field of Classification Search ..... Plt./373
See application file for complete search history.

*Primary Examiner*—Annette H Para
(74) *Attorney, Agent, or Firm*—Klarquist Sparkman, LLP

(57) ABSTRACT

A new and distinct form of *Corydalis* plant characterized by its striking blue green foliage, large yellow flowers, long bloom time, and excellent vigor.

1 Drawing Sheet

Botanical denomination: *Corydalis* hybrid.
Variety designation: 'Canary Feathers'.
Parentage: *Corydalis moorcroftiana*×*Corydalis wilsonii.*

BACKGROUND OF THE INVENTION

The present invention relates to a new and distinct cultivar of *Corydalis,* of the family Papaveraceae, known by the cultivar name, 'Canary Feathers'. This plant originated from planned cross between *Corydalis moorcroftiana,* as the seed parent, and *Corydalis wilsonii,* as the pollen parent. The selection 'Canary Feathers' was made for its blue green foliage, vigor, and multiple repeat blooming stems. This combination of traits is unique in *Corydalis.*

This plant is characterized by:

1. Soft, feathery blue green foliage,
2. Large, yellow, tubular flowers,
3. Repeat blooming,
4. Vigor.

The new variety has been reproduced only by asexual propagation. Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a garden planting of several two-year-old *Corydalis* 'Canary Feathers' in September in Canby, Oreg.

FIG. 2 shows a two year old plant in a growing in a one gallon container in April in Canby, Oreg.

DETAILED PLANT DESCRIPTION

The following is a detailed description of the new *Corydalis* cultivar based on observations of two-year-old specimen grown in a cool greenhouse in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart. The color descriptions are all based on The Royal Horticultural Society Colour Chart.

Plant:
- *Type.*—Herbaceous perennial.
- *Form.*—Clumping.
- *Cold hardiness.*—USDA Zone 6.
- *Size.*—Grows to 20 cm tall to top of foliage and 65 cm wide.
- *Vigor.*—Excellent.
- *Roots.*—Thickened (to 6 mm wide), branching, older roots Brown 200B, younger roots Greyed Yellow 162A.

Stem:
- *Type.*—Fleshy, short, erect.
- *Size.*—Grows to 8 cm long and 5 mm wide.
- *Internodes.*—1 to 3 cm long.
- *Surface texture.*—Glabrous.
- *Color.*—Yellow Green 148C with a pink cast, Greyed Purple 183B.

Leaf:
- *Type.*—Decompound, odd-pinnate and/or lobed.
- *Arrangement.*—Rosette.
- *Shape.*—Narrowly ovate in outline, each leaflet is ovate in outline.
- *Lobing/division.*—7 to 11 leaflets per leaf, leaflets lobed and the bottom leaflets pinnately compound, each lobe entire and mucronate.
- *Venation.*—Pinnate.
- *Margins.*—Entire.
- *Apex.*—Mucronate.
- *Base.*—Cuneate.
- *Blade size.*—Grows to 15 cm long and 9 cm wide.
- *Surface texture.*—Glabrous.
- *Petiole description.*—Grows to 10 cm long and 2.5 mm wide, base clasping, rachis grows to 11 cm long, petiolules grow to 1 cm long, glabrous, color between Yellow Green 152B and Grey Brown 199B, young petioles and petiole bases tinted Greyed Purple 183C.

*Leaf color.*—Top side: Green 139A. Bottom side: closest to Greyed Green 191A.

Inflorescence:

*Type.*—Raceme.

*Number of flowers.*—35 to 45 per raceme.

*Number of raceme in first spring flush.*—15.

*Peduncle description.*—Grows 19 to 25 cm long and 5 mm wide, glabrous, fleshy, Yellow Green 146A with tints of Greyed Purple 183A at base and bract attachments, bracts subtend each pedicel and are simple, entire, rhomboid, cupped, cuspidate, with palmate venation, basal bracts are petiolate with the blades 4 cm long and 2.6 cm wide, terminal bracts are small 1 cm long and 3 mm wide, color is the same as the leaves.

*Pedicel description.*—1 cm long, 0.8 mm wide, Yellow Green 146A tinted Greyed Purple 183A.

*Bloom period.*—April to November in Canby, Oreg. With hot summers this plant may go summer dormant. Blooms best in cool temperatures of spring and fall or in areas with cool night time temperatures. Plants prefer their roots cool to perform their best.

Flower bud:

*Size.*—2.5 cm long and 7 mm wide at the widest point prior to opening.

*Description.*—Shaped like a young tadpole, with the blunt nectary spur curving down slightly.

*Color.*—Yellow 7A with spots of Green 139C on top and bottom lobes.

Flower:

*Type.*—Zygomorphic.

*Corolla description.*—Fleshy, tubular, overall 2.4 cm long and 1.8 cm wide at lip area where it is widest; nectary spur, flattened transversely, extends back from pedicel for 5.5 mm, 5 mm wide and curves slightly down, tube 10 mm long and 5 mm wide; upper petal reflexed 6 mm long and 6 mm wide, hood-like and ridged, entire, ovate, and acute; lower petal is 18 mm long and 8 mm wide, clawed and ridged, reflexed, claw is 11 mm long and grows to 4 mm wide, petal is entire, ovate and acute; the two apically fused inner petals are 9 mm long and 4 mm wide.

*Color.*—Yellow 9A with spots of Green 139C on top and bottom lobes.

*Sepal description.*—2, scarious, 2 mm long and 1.5 mm wide, ovate, entire, acute, Yellow Green 149D.

*Pistil description.*—One, linear and 15 mm long, ovary 11 mm long and Yellow Green 144B, style 3.5 mm long and Yellow Green 150D, stigma is crescent-shaped, 0.5 mm in diameter, Yellow Green 150D.

*Stamen description.*—2, 12 mm long, filaments 11.5 mm long, flat and translucent, Yellow Green 150D, anthers 4, 1.5 mm long, ovoid, Yellow Green 150D, pollen Yellow Orange 16C.

*Fragrance.*—Floral.

*Lastingness.*—A raceme blooms for about 4 weeks on the plant.

Fruit and seed: None, sterile.

Diseases and pests: *Corydalis* species are susceptible to aphids, mites, and rust. This new variety has no known immunities.

COMPARISON TO PARENT PLANTS

Compared to *Corydalis moorcroftiana,* the seed parent, *Corydalis* 'Canary Feathers' has similar flowers but the plant is more fleshy and vigorous, with the foliage thicker and blue green rather than green.

Compared to *Corydalis wilsonii,* the pollen plant, *Corydalis* 'Canary Feathers', is larger, less blue green, and more vigorous. *Corydalis* 'Canary Feathers' blooms longer than either parent.

I claim:

1. A new and distinct form of *Corydalis* plant as hereby illustrated and described.

* * * * *

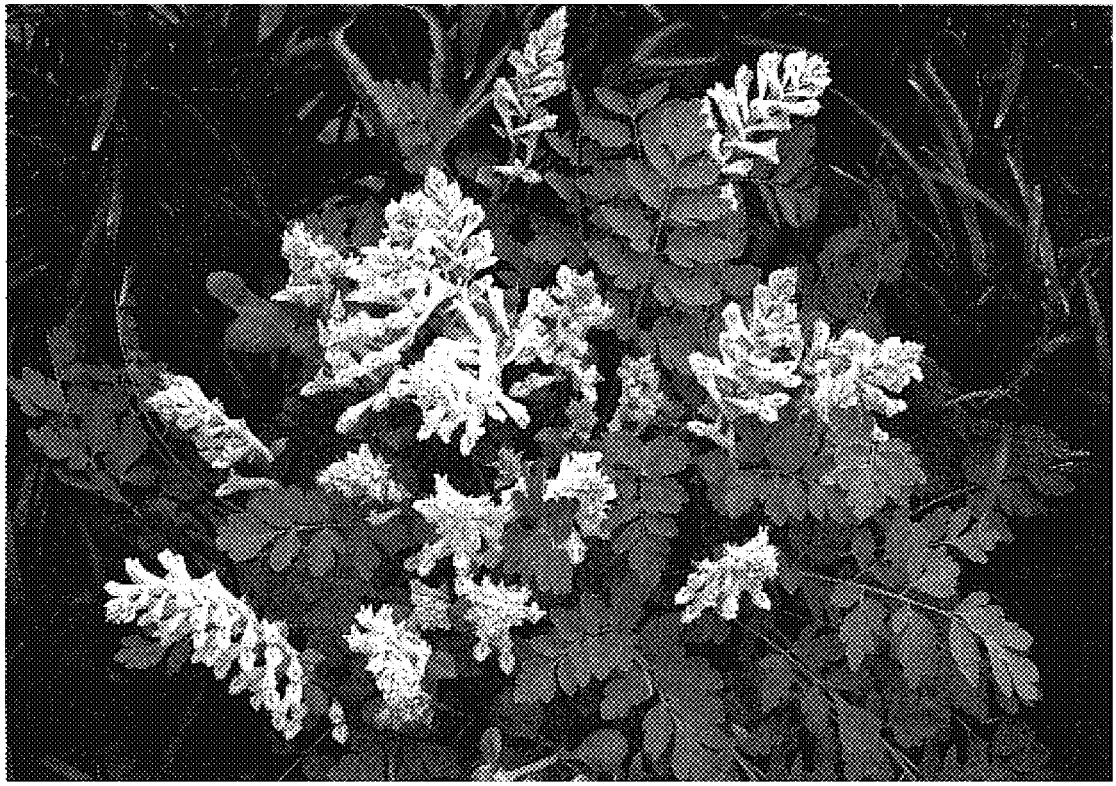

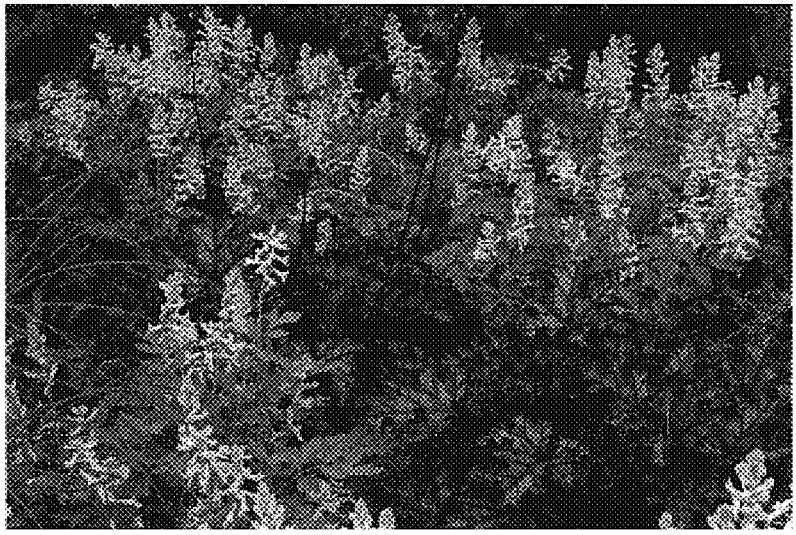
Figure 1 above, figure 2 below.